[19] United States Patent
Berg

[11] 4,066,078
[45] Jan. 3, 1978

[54] DISPOSABLE ELECTRODE

[75] Inventor: Jeffrey Berg, Edison, N.J.

[73] Assignee: Johnson & Johnson, New Brunswick, N.J.

[21] Appl. No.: 655,600

[22] Filed: Feb. 5, 1976

[51] Int. Cl.$^2$ .............................................. A61B 5/04
[52] U.S. Cl. .............................. 128/2.06 E; 128/2.1 E; 128/418; 128/DIG. 4
[58] Field of Search ............... 128/2.06 E, 2.1 E, 404, 128/410, 411, 416–418, DIG. 4

[56] References Cited

U.S. PATENT DOCUMENTS

| | | | |
|---|---|---|---|
| 2,555,037 | 5/1951 | Jensen | 128/417 |
| 3,027,333 | 3/1962 | Friedman | 128/417 X |
| 3,265,638 | 8/1966 | Goodman et al. | 128/417 X |
| 3,518,984 | 7/1970 | Mason | 128/2.06 E |
| 3,547,105 | 12/1970 | Paine | 128/2.06 E |
| 3,565,059 | 2/1971 | Hauser | 128/2.06 E |
| 3,567,657 | 3/1971 | Lichtenstein | 128/417 |
| 3,792,700 | 2/1974 | Sarnoff et al. | 128/2.06 E X |
| 3,911,906 | 10/1975 | Reinhold, Jr. | 128/2.06 E |
| 3,946,730 | 3/1976 | Monter | 128/2.06 E |
| 3,989,050 | 11/1976 | Buchalter | 128/417 |
| 3,993,049 | 11/1976 | Kater | 128/2.06 E |
| 3,994,302 | 11/1976 | Brennen | 128/404 |
| 3,998,215 | 12/1976 | Anderson et al. | 128/2.06 E |

Primary Examiner—Wm. E. Kamm
Assistant Examiner—Lee S. Cohen
Attorney, Agent, or Firm—Steven P. Berman; Robert J. Baran

[57] ABSTRACT

An improved combination electrode for use in medical applications requiring monitoring and stimulation is provided preferably having an electrical current conductor including a connector in addition to a skin-interfacing film wherein this film may have adhesive, plastic and hydrophilic properties such as may reside in an electrically conductive, polymeric composition.

15 Claims, 3 Drawing Figures

DISPOSABLE ELECTRODE

BACKGROUND OF THE INVENTION

Medical electrodes have, in the past, taken many shapes and forms. Principally, they have been shaped according to the use for which they are intended. Electrodes used with monitoring apparatus, such as EKG and EEG machines, commonly have small round contact surfaces, whereas electrodes used with such stimulation apparatus as pain control devices tend to be larger and have rectangularly and other conveniently shaped contact surfaces. Whether intended for monitoring or stimulation use, a design objective for each electrode group has been, and continues to be, good electrical signal transmission between a patient's skin surface and the electrical cables connected to a particular piece of apparatus. With respect to stimulation and monitoring electrodes, efficient signal transmission across the epidermis conductor interface is desirable. Further, with respect to stimulation electrodes, effective signal transmission free of current concentration points or "hot spots" is also desirable.

Of the electrodes presently available, many offer combination structures including a metallic or otherwise conductive support member to which an electrical wire from an associated apparatus may be attached. In many instances, these electrodes need the addition of generous amounts of an electrode paste or gel applied directly to the conductive support member to enhance conductivity across the skin-electrode interface to the point where acceptable operating conditions are achieved. Other prior art electrodes teach the incorporation of an open cellular skin interface pad secured to a conductive support member. This pad as shown in U.S. Pat. No. 3,817,252, is often sponge material which functions to hold an amount of electrolyte solution in order to enhance conductivity across the skin-pad interface. Such an interface pad can be, alternately, saturated with electrode pastes or gels of the type that do run or evaporate as readily as electrolyte solutions.

None of these prior art electrodes offer satisfactory disposable structure, nor do they offer a structure which will maintain constant, efficient and effective electrical transmission for long periods of time without the need for additional electrode paste, gel or solution. Moreover, there is a tendency while using these electrodes, for the electrode gel to separate and/or to flow to a non-uniform thickness. Under these conditions, sections of the conductive support member could be exposed to the skin and local hot spots can result which can cause discomfort if not severe enough to cause burns to the patient's skin.

Prior art electrodes invariably must be secured to the surface of a patient's skin with medical adhesive tape or other securing medium. Very often an electrode secured in this manner will lift off from the skin because of perspiration and/or because of movement by the patient, creating a partial or total interruption in the signal transmission, or causing an uneven current density at the electrode-skin interface.

An objective of this invention, therefore, is to provide an electrode with an electroconductive skin-interface substrate, which will perform a similar function to, and eliminate the need for, an electrolyte solution, electrode paste or electrode gel.

Another objective of this invention is to provide an electrode with a skin-interface substrate having pressure sensitive adhesive properties which will enable the electrode to adhere to the skin without the use of tape or other securing mediums.

Another objective of this invention is to provide an adhesive substrate that has high tack so that minimal pressure is needed to apply it to the skin but is such that it can also be easily separable from the skin upon removal without any noticeable residue.

A further objective is to provide an electrode with a non-liquid skin-interface which is a film which will maintain a uniform thickness and will not separate to expose sections of a conductive support member to the skin.

An even further objective is to provide an electrode having a skin-interface substrate which will not decompose or dry out under long periods of use.

SUMMARY OF THE INVENTION

The objectives of this invention are accomplished in a medical electrode, suitable for stimulation and monitoring applications, including an electrically conductive member capable of being connected to external electro-medical apparatus. This conductive member may be a pliable sheet of material preferably having connected thereto a medium for securing positive electrical connection between the conductive member and the external electro-medical apparatus. Attached to the underside of the conductive member and extending away from the electrical connection is an electrically conductive skin-interface substrate material preferably in the form of a film. This material must have adhesive properties so that it will adhere to the skin of a patient. Preferably, this material also has plastic and hydrophilic properties. A suitable combination of the aforementioned adhesive, plastic and hydrophilic properties is provided by an adhesive composition which comprises an electrically conductive organic polymer plasticized with a polyhydric alcohol. Suitable electrically conductive organic polymers include (1) polymers or copolymers derived from the polymerization of an ester of an $\alpha,\beta$-olefinically unsaturated carboxylic ester and an alcohol having a terminal quaternary ammonium group, and (2) sulfated cellulose esters. The preferred polyhydric alcohol plasticizer is glycerol.

DESCRIPTION OF THE DRAWINGS

The novel features of this invention as well as the invention itself, both as to its organization and method of operation, will best be understood from the following description taken in connection with the accompanying drawings in which like characters refer to like parts, and in which.

DETAILED DESCRIPTION OF THE INVENTION

Medical electrodes are intended for usage as efficient and effective transmission mediums between a patient's skin and an electro-medical apparatus. Primary to their operation is a uniform conductivity through the electrode itself and a uniform conductivity across the electrode skin-interface. Uniform conductivity through an electrode is most often interrupted by a non-uniformity in the electrode material. Uniform conductivity across the electrode-skin interface is most often interrupted by a separation of some or all of the electrode interfacing material in contact with a patient's skin.

The electrode at hand is intended to be disposable. It is also intended to have adhesive properties sufficient to be self-adhering to a patient's skin for approximately 48-120 hours. However, it should contain sufficient flexibility and elasticity to move as a patient's skin moves while returning to original shape when permitted. Additionally, it is intended to provide uniform conductivity with even current densities of approximately 30 microamperes per square millimeter when subjected to a stimulus of about 10-50 milliamperes at 10-350 cycles per second having a pulse duration of about 50-1000 microseconds. This electrode is intended to be easily handled, non-irritating to a patient's skin, and sterilizable.

Figure 1:
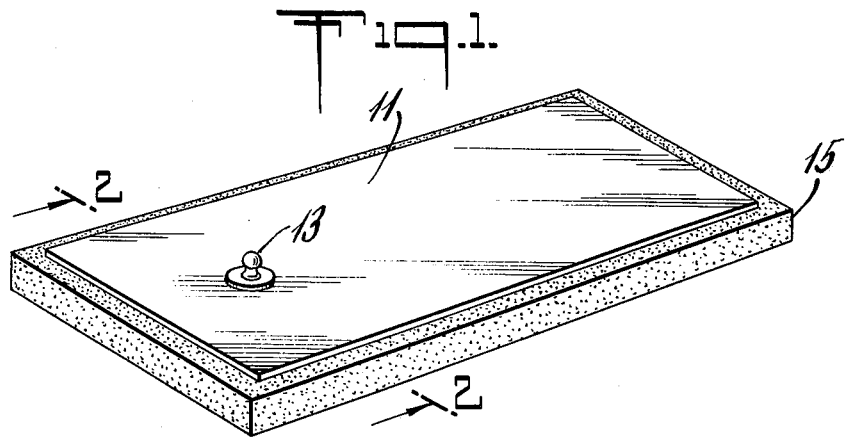
FIG. 1 shows a perspective view of the electrode.

The electrode configuration is shown in FIG. 1. A conductive member 11 is cut, stamped or otherwise shaped out of a piece of conductive material which, in the principal embodiment, is aluminum foil. The shape to which this conductive member 11 is formed will depend upon the particular application in which it is to be used. The shape is sometimes round, but most commonly as shown in FIG. 1, this member 11 is rectangularly shaped. A convenient size for many applications is from about 1½ inches by about 8 inches in size. Alternately, other metallic foils, conductive polymers, graphitized or metalized cloth or wire mesh may be used. For each material, an appropriate strength and thickness is to be chosen to yield a pliable, yet sufficiently strong member 11. When the conductive member 11 is of aluminum foil, it usually is of 1-10 mil thickness.

Secured to the outer surface of the conductive member 11 is a connector 13 for providing a medium to which external signal cables may be attached for electrically communicating with the conductive member 11. This connector 13 may be a conductive swaged snap fastener 13, as shown in the accompanying drawings, which is available commercially. This fastener 13 is riveted or otherwise mechanically and electrically attached to the conductive member 11, extending perpendicularly from the outer surface of this member 11.

Abutting the inner surface of the conductive member 11 is an electrically conductive skin-interface substrate 15. This substrate 15 is a layer of material being typically a film or sheet which will be described below.

Figure 2:
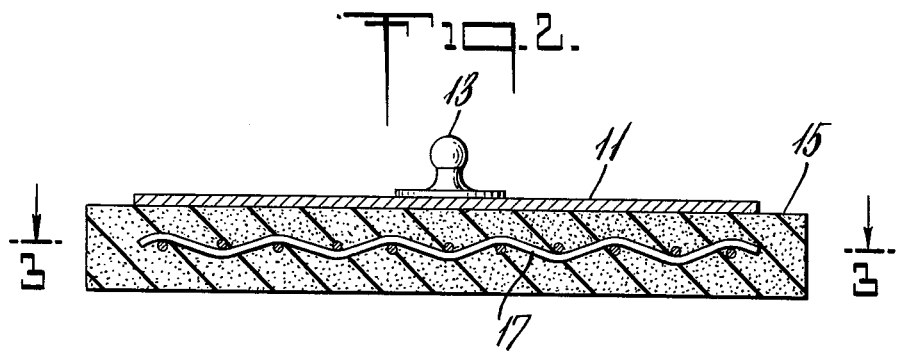
FIG. 2 shows a cross section in side elevation through the electrode of FIG. 1.

The conductive substrate 15 is shaped correspondingly to the conductive member 11. When constructed in combination with a rectangular member 11, the substrate 15 is also rectangular. The film thickness of this substrate 15 is uniform throughout, however, this uniform film may be of various thicknesses. A range of 1/64-¼ inches is common. With the lesser film thicknesses, the substrate 15 coats the surface of the conductive member 11 to its edges, while with greater film thicknesses, the substrate 15 can be extended beyond the edges of the conductive member 11 as illustrated in FIGS. 1 and 2. This extension beyond the edges of the conductive member 11 provides an extra measure of security from the conductive member 11 coming into direct contact with a patient's skin, as well as serving to reduce curling of the edges of the conductive member 11. As will be discussed below, the substrate 15 is a film or sheet having adhesive properties, thus when it is brought into contact with the conductive member 11, it will adhere to that member 11 providing electrical connection with it.

A diffusion screen 17, FIG. 2 may be used in electrode configurations where a greater thickness substrate 15 film is used. This diffusion screen 17, while not a necessary part of the electrode, will tend to further distribute current densities throughout the substrate 15 which can result in a more uniform density of current at the substrate 15 surface in contact with a patient's skin. A further advantage to the use of this screen 17 is that it acts to reenforce and strengthen the substrate 15.

Figure 3:
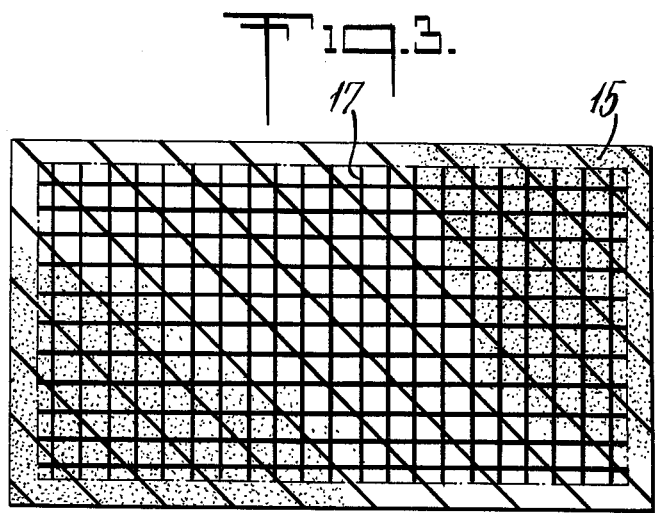
FIG. 3 shows a plan elevation cross section through the skin-interfacing film of the electrode of FIG. 1.

The screen 17 is positioned midway through the thickness of the substrate 15, in alignment with the conductive member 11, and is of a size to extend completely under the conductive member 11. The screen 17, FIG. 3, can be a metal, such as 316 stainless steel, or a metalized fabric of the type which is flash vaporized with aluminum particles. Typically, this screen can be of a size having 4½ to 13 courses per inch.

In operation, the electrode is applied with the substrate 15 in direct contact with the skin. The adhesive properties of the substrate 15 eliminate the necessity for tape or other securing mediums to hold the electrode in continuous contact with the skin. The swaged fastener 13, or other suitable connector, receives electrical signals from an external apparatus. These signals are conducted into the conductive member 11 which in turn directly conducts them into the substrate 15. In this manner, current densities are uniformly distributed over the area of the substrate 15 in contact with the conductive member 11 and, in turn, are uniformly transmitted to the skin surface in contact with the substrate 15.

Primary to the unique structure of the electrode for eliminating the need for added electrode pastes, gels or electrolyte solutions, and for eliminating the need for securing mediums to hold the electrode in place, is the composition and structure of the substrate 15 material, enabling it to possess the desired physical, chemical and electrical properties.

Substrate 15 is a sheet or film of an electrically conductive organic polymer plasticized with a polyhydric alcohol, preferably glycerol.

One example of an electrically conductive organic polymer which is suitable for use in substrate 15 is a hydrocolloidal material disclosed in copending application Ser. No. 509,207 entitled "Hydrophilic Random Interpolymer Compositions and Method for Making Same", filed Sept. 25, 1974, the teachings of which copending application are hereby specifically incorporated by reference. These hydrophilic random interpolymers have a capacity for absorbing and retaining large amounts, for example 10-125 times their own weight, of water. The cross-linked random hydrophilic interpolymer compositions useful as components in substrate 15 may be prepared in accordance with the methods described in the above mentioned copending application. The composition of the random hydrophilic interpolymers may be the same as the compositions disclosed in Ser. No. 509,207, that is, the interpolymers may comprise: (A) from about 10 parts by weight to about 90 parts by weight of an ester of an $\alpha,\beta$-olefinically unsaturated carboxylic acid and a monohydric or polyhydric alcohol having a terminal quaternary ammonium group, and (B) correspondingly, from about 90 parts by weight to about 10 parts by weight of at least one $\alpha,\beta$-olefinically unsaturated comonomer, and (C) at least 0.02 parts by weight of a cross-linking agent comprising a difunctional monomer.

In addition to the aforementioned interpolymer compositions it is also possible to use as the polymeric component of substrate 15 random interpolymers which include 100 parts by weight of an ester of an α,β-olefinically unsaturated carboxylic acid and a monohydric or polyhydric alcohol having terminal quaternary ammonium group and at least 0.02 parts by weight of a difunctional cross-linking agent. The latter mentioned random interpolymers are similar in composition to the first mentioned random interpolymer, except, of course, that the latter class of polymers does not include the α,β-olefinically unsaturated comonomers which are found in the first class of interpolymers. Both classes of polymer compositions can be prepared by the method outlined in Ser. No. 509,207.

In accordance with this aspect of the invention, the random interpolymer esters form a colloidal dispersion or suspension in water. Glycerol or another polyhydric alcohol is added to the continuous phase to enhance plasticity and hydrophilicity. This form of the substrate 15 may be prepared by casting the hydrocolloidal material, described above, into shallow trays for drying. Heating to 120° F for a given period of time, depending upon concentration and composition will hasten the formation of the hydrocolloid into an elastic and plastic film or sheet. The thickness of this film or sheet is determined by the concentration of solids and the depth of pool of the hydrocolloidal material cast.

The composition and processing yields a material of sufficient thickness to be a sheet and not a film of material. The physical integrity of a sheet of material, with its shape retention and elasticity, is desirable to the electrode structure and operation.

While as previously mentioned, the above disclosed interpolymers will absorb large amounts of water, they are not completely insoluble in water due to the fact that they contain at least 0.02 parts by weight per 100 parts of monomer of a difunctional cross-linking agent.

A second example of an electrically conductive organic polymer suitable for use in preparing substrate 15 is an alkali salt of a sulfated cellulose ester. The sulfated cellulose ester may be prepared as set forth in U.S. Pat. No. 3,897,782 issued Aug. 15, 1975, the teachings of which patent are hereby specifically incorporated by reference.

The sulfated cellulose ester is selected from the group consisting of alkali cellulose ester sulfates wherein the acyl group comprises from 1 to 6 carbon atoms; more preferably the acyl group comprises from 1 to 4 carbon atoms.

Examples of these resins are such alkali cellulose ester sulfates as sodium, potassium or lithium cellulose acetate sulfate, sodium, potassium or lithium cellulose acetate-butyrate sulfate, sodium cellulose propionate sulfate and potassium cellulose butyrate sulfate.

It has been discovered that these resins exhibit the unusual properties of retaining their tensile strength in salt solutions such as body fluids while readily dispersing in tap water. It has further been discovered that these unique properties are a function of the degree of sulfate substitution which expresses the average number of sulfate groups per anhydroglucose unit of the cellulosic ester. In general, by reducing this factor in a particular resin it will exhibit decreasing dispersibility in water and increasing strength in salt solutions. A more detailed discussion of this composition may be obtained from a reading of the Body Fluid Barrier Films patent disclosure referenced above.

The substrate 15 compositions exhibit a tackiness which can be increased as the glycerol concentration is increased. As water and/or salt water is absorbed the surface of the substrate material 15 softens. As a result, the substrate 15 will flow into pores and other irregularities in the skin, creating a mechanical-interlock bond with the skin in addition to the already present adhesive bond. The bonding and, concomitantly, the electrical transmission of the electrode are enhanced as it "ages" in contact with the skin.

The flow condition eliminates air spaces between the skin and the substrate 15 to greatly reduce the impedance across the interface. This in turn greatly reduces the heat normally created at this interface. While the surface portion of the substrate 15 will flow, the greater portion of its mass will remain intact. Thus, the material resists separation or the development of irregular thicknesses. As a result, two heat and/or burn producing conditions, i.e., a high resistance across the interface due to an air layer which creates high temperatures over the entire interface, and the physical contact of the conductive member 11 directly to the skin creating a shunt of the current to a small area and generating extreme temperature in that area, are avoided.

A secondary electrical effect is also improved as the electrode "ages". Present during the operation of all electrodes is a battery effect created at the skin interface due to the capacitance across this interface. This battery effect causes some current to tend to circle backward towards its source of flow creating eddy currents. With this electrode of the invention, as water and body salts are absorbed into the electrode substrate, the interface area becomes more ionically, i.e. electrically, homogenous thus reducing the battery effect and any resulting eddy currents.

The electrode may be packaged for use in a sealed sterilized envelope of any of a number of suitable materials such as polyethylene. A release paper of the waxed or plastic coated type can be used to protect the substrate 15 before application to a skin surface.

Since many changes and many embodiments could be made to the above-described invention without departing from the scope thereof, it is intended that all matter contained in the above description be interpreted as illustrative and not in the limiting sense.

What is claimed:

1. An electrode providing electrical contact with a patient's skin comprising:
    a conductive member including means for connection to an external electrical apparatus; and
    means for electrically interfacing to said patient's skin being electrically and mechanically connected to said conductive member, said interfacing means being a non-liquid film which is easily separable from the skin upon removal without any noticeable residue and which consists essentially of an electrically conductive organic polymer plasticized with a polyhydric alcohol with said organic polymer being derived from an ester of an α,β-olefinically unsaturated carboxylic acid and a monohydric or polyhydric alcohol having a terminal quaternary ammonium group.

2. The electrode of claim 1 wherein said interfacing means is of sufficient thickness to constitute a sheet of material.

3. The electrode of claim 1 wherein said polyhydric alcohol is glycerol.

4. The electrode of claim 1 wherein said interfacing means is an adhesive sheet adherent to said conductive member.

5. The electrode of claim 4 wherein said adhesive sheet contains a diffusion screen located within said sheet and in alignment with said conductive member.

6. The improved electrode of claim 4 wherein said sheet is pliable and hydrophilic.

7. The electrode of claim 1 wherein said interfacing means is an adhesive film adherent to said conductive member.

8. The electrode of claim 7 wherein said film is pliable and hydrophilic.

9. The electrode of claim 1 wherein said interfacing means is further characterized as providing uniform conductivity with even current densities of approximately 30 microamperes per square millimeter when subjected to a stimulus of about 10–50 milliamperes at 10–350 cycles per second having a pulse duration of about 50–1000 microseconds.

10. The electrode of claim 1 wherein said plasticized organic polymer comprises (A) from about 10 parts by weight to about 90 parts by weight of an ester of an $\alpha,\beta$-olefinically unsaturated carboxylic acid and a monohydric or polyhydric alcohol having a terminal quaternary ammonium group, and (B) correspondingly, from about 90 parts by weight to about 10 parts by weight of at least one $\alpha,\beta$-olefinically unsaturated co-monomer, and (C) at least 0.02 parts by weight of a cross-linking agent comprising a difunctional monomer.

11. An electrode providing electrical contact with a patient's skin comprising:
a conductive member including means for connection to an external electrical apparatus; and
means for electrically interfacing to said patient's skin being electrically and mechanically connected to said conductive member, said interfacing means being a non liquid film which is easily separable from the skin upon removal without any noticeable residue and which consists essentially of an electrically conductive organic polymer plasticized with a polyhydric alcohol, said plasticized organic polymer comprising a sulfated cellulose ester.

12. The electrode of claim 11 wherein said sulfated cellulose ester is selected from the group consisting of alkali cellulose ester sulfates wherein the acyl group comprises from 1 to 6 carbon atoms.

13. The electrode of claim 11 wherein said interfacing means being further characterized as providing uniform conductivity with even current densities of approximately 30 microamperes per square millimeter when subjected to a stimulus of about 10–50 milliamperes at 10–350 cycles per second having a pulse duration of about 50–1000 micro-seconds.

14. An electrode providing electrical contact with a patient's skin comprising:
a conductive member including means for connection to an external electrical apparatus; and means for electrically interfacing to said patient's skin being electrically and mechanically connected to said conductive member, said interfacing means consisting essentially of an electrically conductive organic polymer plasticized with a polyhydric alcohol with said organic polymer including quaternary ammonium groups.

15. An electrode providing electrical contact with a patient's skin comprising:
a conductive member including means for connection to an external electrical apparatus; and means for electrically interfacing to said patient's skin being electrically and mechanically connected to said conductive member, said interfacing means consisting essentially of an electrically conductive organic polymer plasticized with a polyhydric alcohol with said organic polymer including sulfate groups.

* * * * *